US011311278B2

(12) United States Patent
Peliks

(10) Patent No.: US 11,311,278 B2
(45) Date of Patent: Apr. 26, 2022

(54) TISSUE REMOVAL DEVICE AND METHOD OF USE

(71) Applicant: MERIT MEDICAL SYSTEMS, INC., South Jordan, UT (US)

(72) Inventor: Robert Bilgor Peliks, San Francisco, CA (US)

(73) Assignee: Merit Medical Systems, Inc., South Jordan, UT (US)

( * ) Notice: Subject to any disclaimer, the term of this patent is extended or adjusted under 35 U.S.C. 154(b) by 365 days.

(21) Appl. No.: 15/816,856

(22) Filed: Nov. 17, 2017

(65) Prior Publication Data

US 2018/0092633 A1  Apr. 5, 2018
US 2022/0054112 A9  Feb. 24, 2022

Related U.S. Application Data

(63) Continuation of application No. PCT/US2016/035138, filed on Jun. 1, 2016.

(60) Provisional application No. 62/326,785, filed on Apr. 24, 2016, provisional application No. 62/169,888, filed on Jun. 2, 2015.

(51) Int. Cl.
A61B 10/02 (2006.01)

(52) U.S. Cl.
CPC ...... *A61B 10/0266* (2013.01); *A61B 10/0283* (2013.01); *A61B 2010/0208* (2013.01)

(58) Field of Classification Search
None
See application file for complete search history.

(56) References Cited

U.S. PATENT DOCUMENTS

| 4,817,631 | A | 4/1989 | Schnepp-Pesch et al. |
| 5,152,792 | A * | 10/1992 | Watkins ............ A61B 17/8847 606/87 |
| 5,324,300 | A | 6/1994 | Elias et al. |
| 5,392,790 | A | 2/1995 | Kanner et al. |
| 5,713,368 | A | 2/1998 | Leigh |
| 6,086,543 | A | 6/2000 | Anderson et al. |
| 6,440,086 | B1 | 8/2002 | Hohenberg |
| 2002/0077648 | A1 | 6/2002 | Lee et al. |
| 2006/0224082 | A1 | 10/2006 | Vetter et al. |
| 2009/0209854 | A1 * | 8/2009 | Parihar ............... A61B 90/39 600/431 |
| 2009/0318832 | A1 | 12/2009 | Andreyko et al. |
| 2010/0204611 | A1 | 8/2010 | Zambelli |
| 2010/0262166 | A1 * | 10/2010 | Boraiah ............... A61B 17/34 606/148 |
| 2011/0004120 | A1 | 1/2011 | Drubetsky |
| 2013/0053725 | A1 | 2/2013 | Beck et al. |

(Continued)

FOREIGN PATENT DOCUMENTS

| WO | 2009059236 | 5/2009 |
| WO | 2012167216 | 12/2012 |

OTHER PUBLICATIONS

International Search Report of related Patent Application No. PCT/US2016/035138 dated Aug. 31, 2016.

(Continued)

*Primary Examiner* — Jay B Shah
(74) *Attorney, Agent, or Firm* — Stoel Rives LLP

(57) ABSTRACT

A biopsy device for acquiring a tissue sample is disclosed. The biopsy device comprises a tissue-engaging outer element, a handle and a trocar. Multiple tissue samples may be collected.

11 Claims, 6 Drawing Sheets

(56) References Cited

U.S. PATENT DOCUMENTS

2013/0131548 A1  5/2013  McGhie et al.
2013/0237877 A1  9/2013  Rethy et al.
2013/0331734 A1  12/2013 Keast et al.
2014/0207021 A1  7/2014  Snow
2015/0065912 A1  3/2015  Peliks

OTHER PUBLICATIONS

Written Opinion of the International Searching Authority of related Patent Application No. PCT/US2016/035138 dated Aug. 31, 2016.
European Search Report dated Sep. 26, 2018 for EP16804272.9.

* cited by examiner

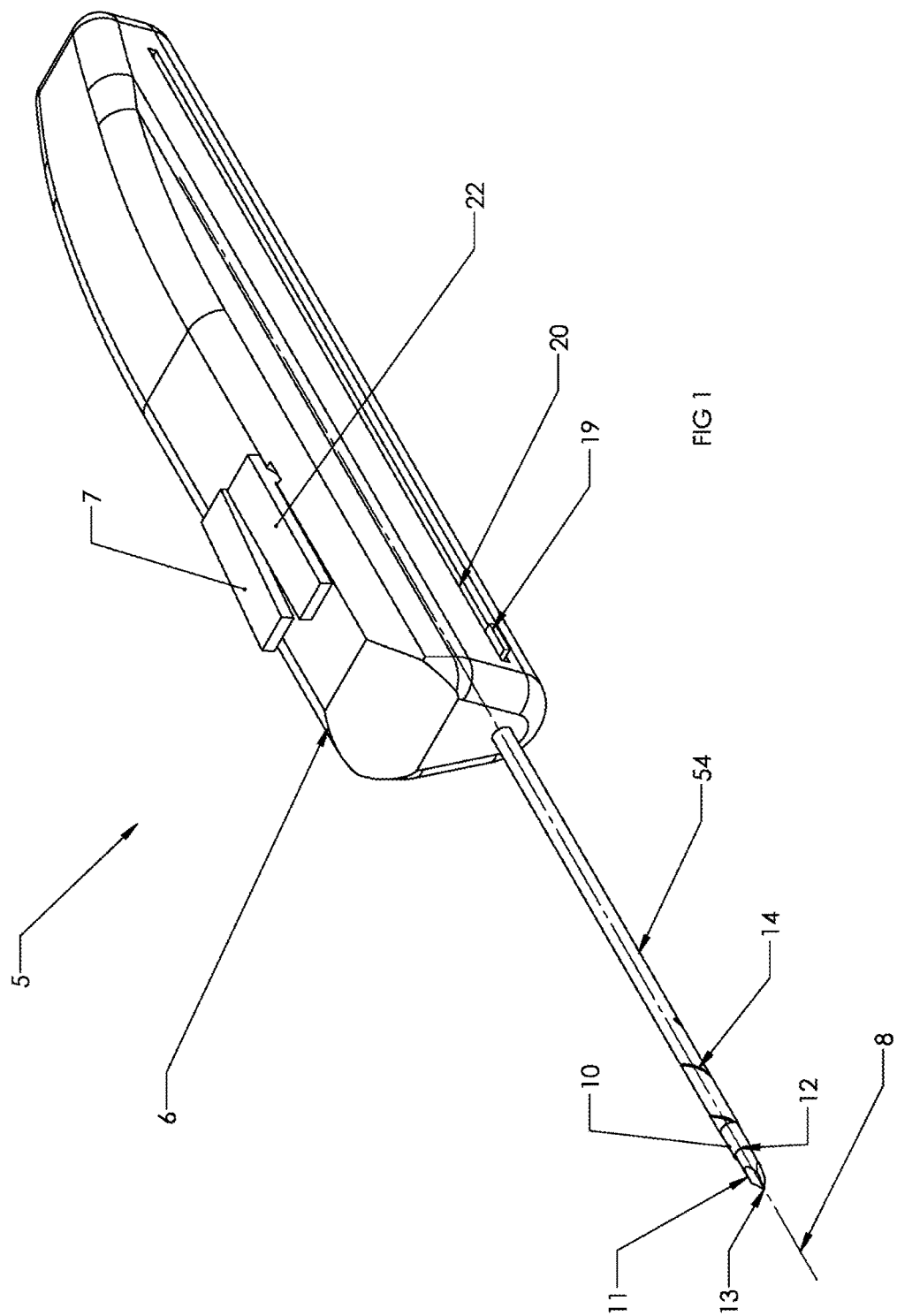

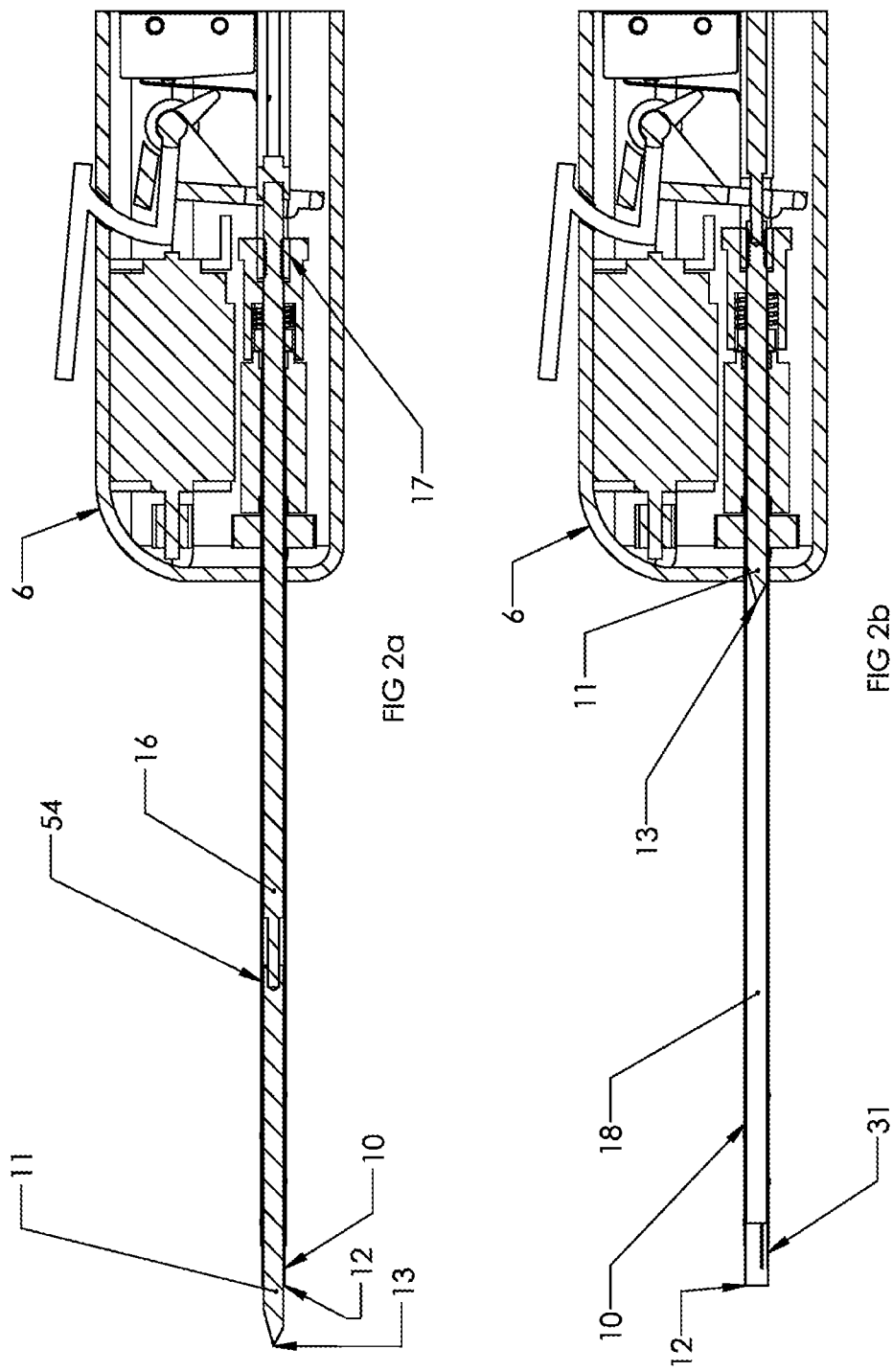

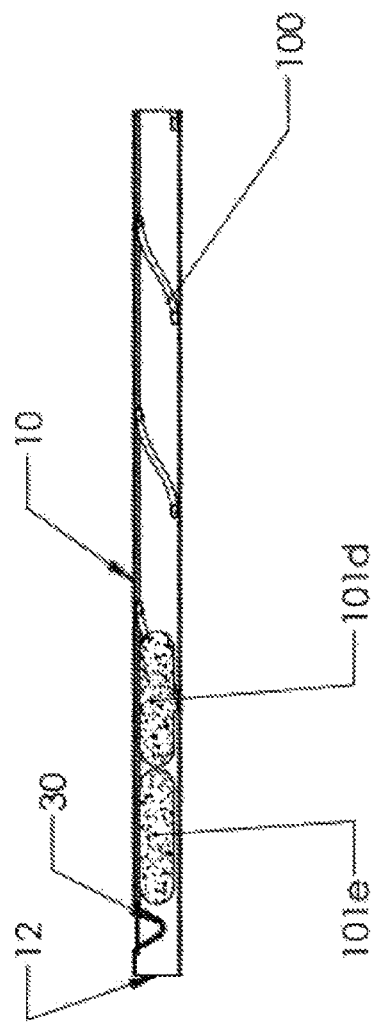

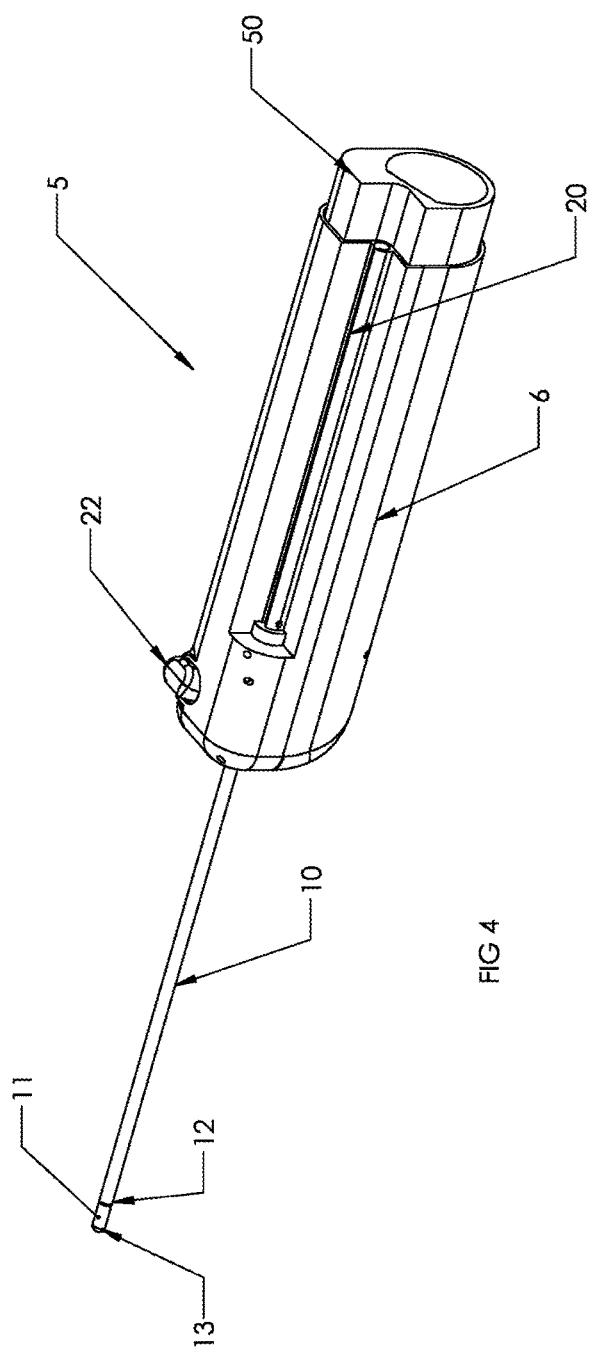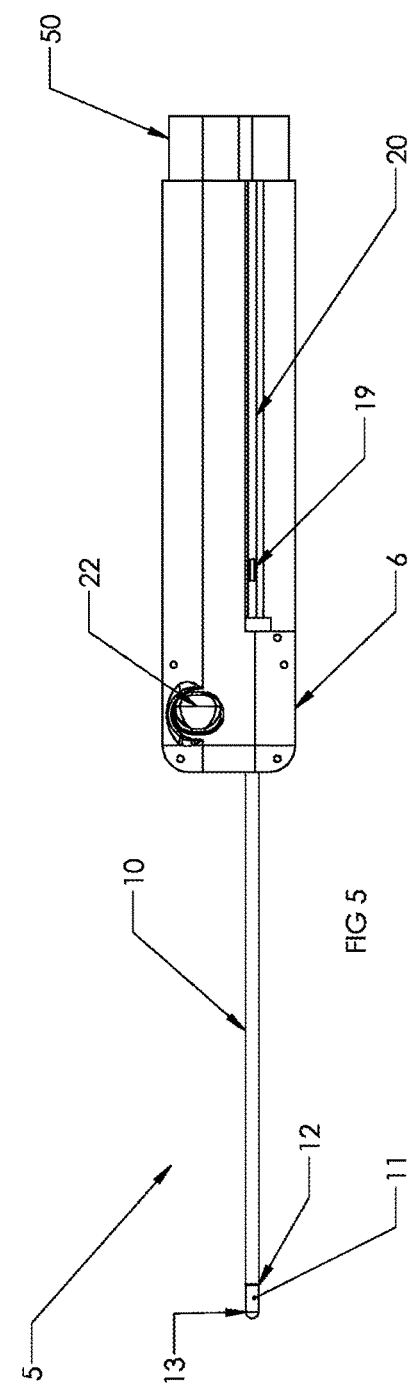

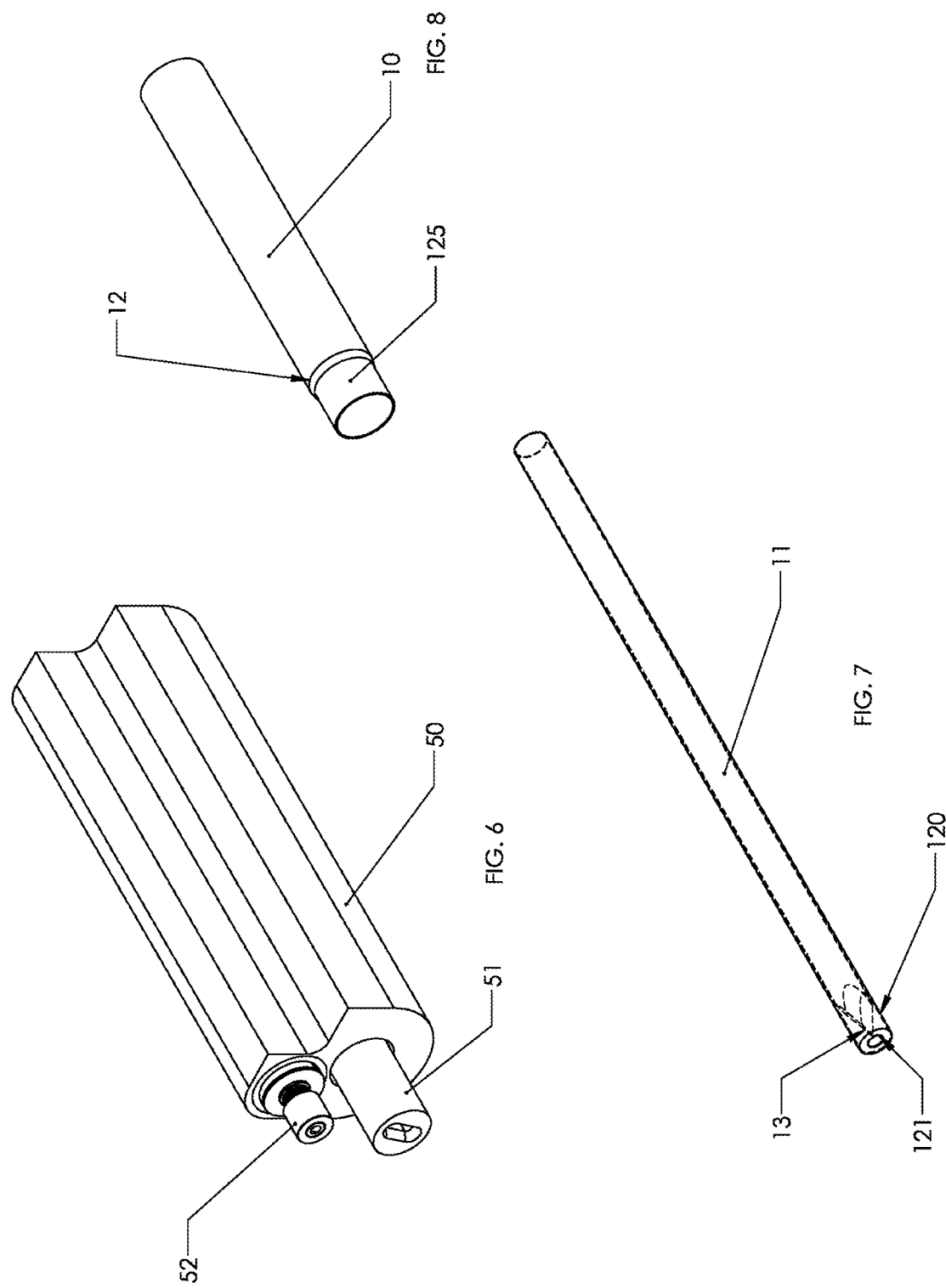

TISSUE REMOVAL DEVICE AND METHOD OF USE

CROSS-REFERENCE TO RELATED APPLICATIONS

This application is a continuation of International Application No. PCT/US2016/035138, filed on Jun. 1, 2016, which claims benefit of U.S. Provisional Application Nos. 62/169,888 filed on Jun. 2, 2015 and 62/326,785 filed on Apr. 26, 2016, which are both incorporated by reference herein in their entireties.

BACKGROUND OF THE INVENTION

Field of the Invention

This disclosure relates to medical instrumentation. More particularly, a tool used for acquiring tissue and a method for using the same are disclosed.

Description of the Prior Art

A number of medical procedures require the removal of tissue samples from a patient. These operations can range from the removal of suspicious tissue, as in the biopsy of a cancerous lesion, to cell harvesting, as in a bone marrow donation. A number of different biopsy tools are used for retrieving these tissue samples from patients. There are two main styles of core biopsy tools—side cutting and forward coring. One style of biopsy tool may be called forward coring. A forward coring biopsy tool may include a spinning cannula with a razor edge. As the device is advanced into a tissue mass, the cannula may core the tissue. The cored tissue sample must then be parted off from the remaining tissue mass. There are a number of methods for parting off the tissue sample, such as tearing or cutting.

SUMMARY OF THE INVENTION

A tool used to obtain tissue samples is disclosed herein. The partoff mechanism of the tool can be comprised of at least one tubular element. The tubular element may be spun along a central axis. The distal end of the tubular element may comprise a flexible partoff tab. The angle of this partoff tab may be adjusted during use. For example, the partoff tab may be flush with the remainder of the tube wall while advancing the device into a mass of tissue & while coring a tissue sample; the partoff tab may be angled inwards to partoff the sample from the tissue mass. The tube may be spinning as the partoff tab is repositioned; if the tube is spinning, the partoff tab may cut the tissue mass as it is being repositioned. The partoff tab may remain positioned inwards to secure the samples within the tubular element (e.g. the partoff tab may prevent the samples from falling out of the terminal distal end of the tubular element).

A tool for acquiring tissue is disclosed. The tool can have a cutter tube comprising a tubular system and a partoff tab. The partoff tab may have a partoff tab first end and a partoff tab second end. The partoff tab first end can be secured to the tubular system. The partoff tab second end can be secured to the tubular system. The cutter tube can have a tubular longitudinal axis. The partoff tab can have a longitudinally expanded configuration and a longitudinally contracted configuration. The length of the partoff tab along the tubular longitudinal axis in the longitudinally expanded configuration may be longer than the length of the partoff tab in the longitudinally contracted configuration.

A tool for acquiring tissue may be comprised of a cutter tube, a partoff tab having a partoff tab first and second ends and an actuator. The partoff tab first end can be secured to the cutter tube. The partoff tab second end can be secured to the actuator. The length of the partoff tab along the tubular longitudinal axis in the longitudinally expanded configuration may be longer than the length of the partoff tab in the longitudinally contracted configuration.

A tool for acquiring tissue may comprise a cutter tube. The cutter tube may comprise the tubular system and the partoff tab. The length of the partoff tab along a tubular longitudinal axis in the longitudinally expanded configuration may be longer than the length of the partoff tab in the longitudinally contracted configuration. The partoff tab can have two flex points, when in the contracted configuration.

A tool for acquiring tissue may comprise a cutter tube. The cutter tube may comprise the tubular system and the partoff tab. The length of the partoff tab along a tubular longitudinal axis in the longitudinally expanded configuration may be longer than the length of the partoff tab in the longitudinally contracted configuration. The partoff tab can has one inflection point, when in the contracted configuration.

A tool for acquiring tissue may comprise a cutter tube, a partoff tube and an actuator. The partoff tab can have two flex points, when in the contracted configuration.

A tool for acquiring tissue may comprise a cutter tube, a partoff tube and an actuator. The partoff tab can has one inflection point, when in the contracted configuration.

A method for operating a mass removal device is disclosed. The mass removal device may comprise a cutter tube, comprising the tubular system and the partoff tab. The partoff tab can have a partoff tab first end and a partoff tab second end. The partoff tab first end can be secured to the tubular system. The partoff tab second end can be secured to the tubular system. The method can comprise actuating the partoff tab, wherein the actuating comprises extending the partoff tab radially inwardly or outwardly relative to the cutter tube.

A method for operating a mass removal device is disclosed. The mass removal device may comprise a cutter tube, an actuator and a partoff tab. The partoff tab can have a partoff tab first end and a partoff tab second end. The partoff tab first end can be secured to the cutter tube. The partoff tab second end can be secured to the actuator. The method can comprise actuating the partoff tab, wherein the actuating comprises extending the partoff tab radially inwardly or outwardly relative to the cutter tube.

A method for operating a mass removal device is disclosed. The mass removal device may comprise a cutter tube, an actuator and a partoff tab. The partoff tab can have a partoff tab first end and a partoff tab second end. The partoff tab first end can be secured to the cutter tube. The partoff tab second end can be secured to the actuator. The method can comprise actuating the partoff tab, wherein the actuating comprises extending the partoff tab radially inwardly or outwardly relative to the cutter tube. The cutter tube may rotate relative to the tissue mass. The mass removal device may acquire multiple samples with one single insertion into the tissue mass. The samples may stack up sequentially within the cutter tube.

BRIEF DESCRIPTION OF THE DRAWINGS

FIG. 1 is an isometric view of a variation of the tool.

FIG. 2a and FIG. 2b illustrate a cross-sectional view of the tool along a tubular longitudinal axis 8. FIG. 2a illustrates the tool with the trocar out (insertion mode) and FIG. 2b illustrates the tool with the trocar back (sampling mode).

FIG. 3 is a cross-sectional view of the distal section of the cutter tube with a tissue-engaging inner element.

FIG. 4 is an illustrative isometric view of a variation of the tool

FIG. 5 is a top view of a variation of the tool.

FIG. 6 is an illustrative isometric view of a variation of the reusable handle.

FIG. 7 is an illustrative isometric view of a trocar recessed with a trocar tube.

FIG. 8 is an illustrative isometric view of an inner tube extending distally past the cutter tube terminal distal end.

DETAILED DESCRIPTION

Figure 9:
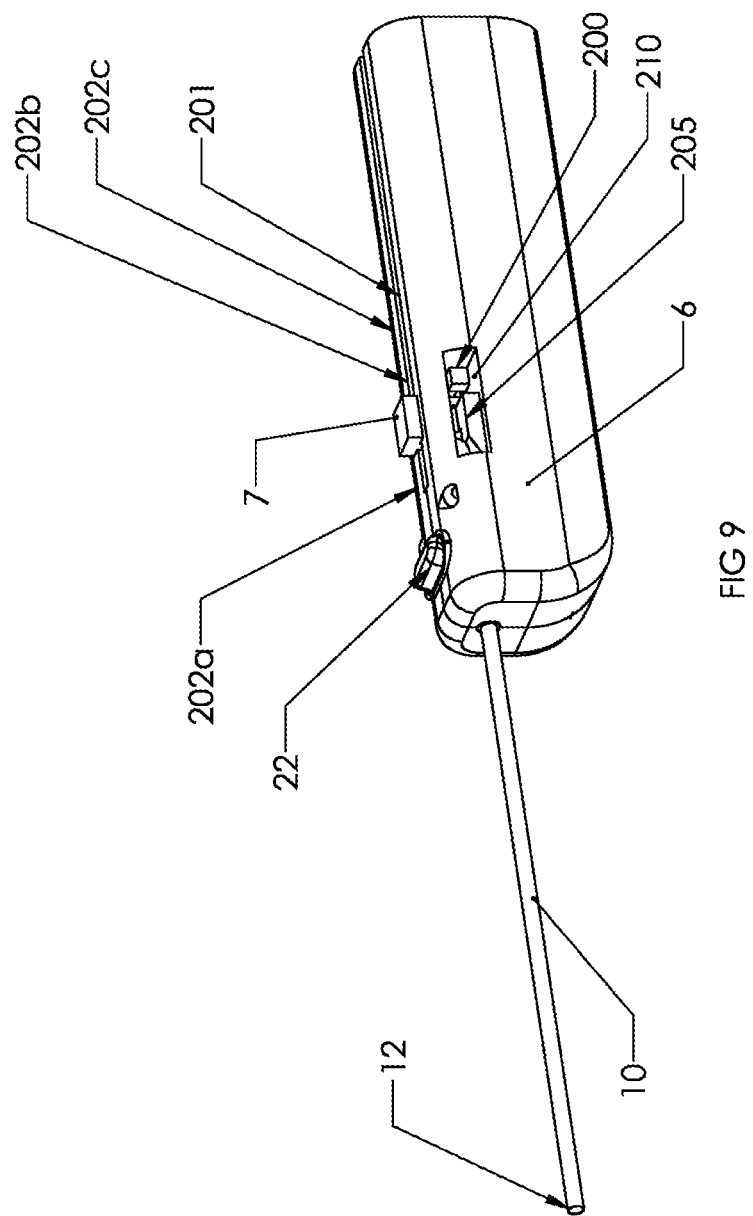
FIG. 9 is an illustrative isometric view of a handle with a slideable button.

FIG. 1 illustrates a tool 5 that can be sterilized. The tool 5 may have an ergonomic handle 6. The handle 6 can have a handle top portion joined together with a handle bottom portion. The tool 5 may have a handle left portion and a handle right portion. The handle top portion and the handle bottom portion may be injection molded. The handle 6 may contain a cutter tube 10. The cutter tube 10 can be rotatable about a tubular longitudinal axis 8 or rotationally-fixed with respect to the handle 6. The cutter tube 10 can be longitudinally fixed with respect to the handle 6. The cutter tube 10 can extend distally from the handle 6 and can have a cutter tube terminal distal end 12. The handle 6 can have an electrical connection which can connect to an external power supply. The tool 5 could instead, or in combination with an external power supply, be powered with internal batteries, mechanically, hydraulically or pneumatically. A cover may enclose the samples in a collection chamber. The cover may be removed or adjusted to provide physical access to the samples stored in the collection chamber. The cover can be transparent, translucent, or opaque. The rotation of the cutter tube 10 may be controlled by actuating a first button 22. A second button 7 may actuate a partoff mechanism 31. The second button 7 and the first button 22 may be the same button; for example, a button could have multiple positions and depending on the position may actuate the partoff mechanism 31 and/or rotate the cutter tube 10. The first button 22 and/or the second button 7 could be used to rotate the cutter tube 10 in different directions (e.g., clockwise and counter-clockwise). The first button 22 and/or the second button 7 could be used to control the position of a trocar 11. The trocar 11 could have a sharp point; for example, the trocar 11 could be formed by three facets; the three facets could form a trocar point 13 at the distal terminal end of the trocar 11. The trocar point 13 could be soft and/or atraumatic. The trocar point 13 could be rounded, chamfered, square and/or beveled. The trocar 11 could be rigid and/or flexible. The trocar 11 could be made from one solid piece of material (e.g., stainless steel or plastic). The trocar 11 could be made from two or more components; for example a portion of the trocar 11 could have different properties than the remainder. For example, one section of the trocar 11 could be rigid and another section could be flexible. For example, the distal end of the trocar 11 could feature a sharp trocar point and be made from a rigid material such as stainless steel; for example, the proximal end of the trocar 11 could be made from a flexible material. For example, a flexible portion of the trocar 11 could be made from a soft polymer. The flexible portion of the trocar 11 could be made from a flexible assembly of rigid components, such as a chain and/or ball chain. One section of the trocar 11 could rotate with respect to another section of the trocar 11. For example, the distal end of the trocar 11 could rotate with cutter tube 10, while another section of the trocar 11 could be rotationally stationary with respect to the handle 6. The trocar 11 could be positioned concentrically inside of the cutter tube 10. The gap between the outside diameter of the trocar 11 and the inside diameter of the cutter tube 10 could be a clearance fit, such as between 0.001 to 0.006 in (0.02 to 0.15 mm). The trocar point 13 could extend past the cutter tube terminal distal end 12 to enable easier insertion into a tissue. A coaxial introducer 54 may be secured to the handle 6. The coaxial introducer 54 may be comprised of a tube and a luer fitting. The luer fitting of the coaxial introducer 54 may secure the coaxial introducer 54 to the handle 6. The coaxial introducer 54 may be secured to the handle 6 using a latch mechanism and/or magnet. The coaxial introducer 54 may be secured to the handle 6 without rotating the coaxial introducer 54 with respect to the handle 6. The tube of the coaxial introducer 54 may have a clearance fit with the cutter tube 10. For example, the gap between the cutter tube 10 and the coaxial introducer 54 may be between 0.001 to 0.006 in (0.02 to 0.15 mm). The trocar 11, the cutter tube 10 and/or the coaxial introducer 54 could use radiofrequency (RF) energy to assist in cutting. For example, the first button 22, the second button 7 and/or a third button could be used to control the RF energy. RF energy could be turned on to assist during insertion of the probe into the tissue and/or during sampling/partoff of a tissue sample. The trocar 11 could spin relative to the handle 6 about the tubular longitudinal axis 8. The trocar 11 could be rotationally fixed relative to the handle 6. The cutter tube 10 and/or the coaxial introducer 54 could have a lubricious coating. For example, the outside diameter of the cutter tube 10 and/or the coaxial introducer 54 could be coated to adjust friction with Teflon, parylene, a hyrodophilic coating, and/or a hydrophobic coating. The outside diameter of the cutter tube 10 and/or the coaxial introducer 54 could be engineered to adjust friction, such as being polished, having microscaffolds, and/or plasma activation. outside diameter of the cutter tube 10 and/or the coaxial introducer 54 could be modified to reduce the friction to less than about 0.1, or more narrowly, less than about 0.05. The coaxial introducer 54 could be longitudinally fixed and/or rotationally fixed to the handle 6. The coaxial introducer 54 could translate and/or rotate with respect to the handle 6. Depressing a button, such as the first button 22 and/or the second button 7, could move the coaxial introducer 54 and/or the cutter tube 10. For example, when coring tissue, the coaxial introducer 54 could retract relative to the cutter tube 10 (or the cutter tube 10 could advance relative to the coaxial introducer 54), thereby exposing the cutter tube terminal distal end 12. After coring, the cutter tube terminal distal end 12 could be recessed underneath a distal end of the coaxial introducer 54. For example, during tissue partoff and/or tissue transport, the cutter tube terminal distal end 12 could be recessed to allow the cutter tube 10 to spin without risking coring and/or cutting additional tissue.

During insertion of the tool 5 into the tissue and/or while obtaining a tissue sample, the cutter tube 10, the coaxial introducer 54 and/or the trocar 11 could spin about the tubular longitudinal axis 8. Spinning the cutter tube 10, the coaxial introducer 54 and/or the trocar 11 could result in a lower and/or more consistent resistance to advancing the tool. For example, even if the resistance is not lower, it may be made more consistent by minimizing the stick-slip friction phenomenon. The rotational velocity of the spinning the cutter tube 10, the coaxial introducer 54 and/or the trocar 11 could be variable; for example, the velocity could be dependent on the tissue type, the rate of advancement of the tool, the state of the tool (e.g., insertion, coring and/or partoff), and/or the temperature. The rotational velocities of the spinning the cutter tube 10, the coaxial introducer 54 and/or the trocar 11 could all be different and/or the same as each other. The rotational velocities of the spinning the cutter tube 10, the coaxial introducer 54 and/or the trocar 11 could be controlled with separate motors. The rotational velocities of the spinning the cutter tube 10, the coaxial introducer 54 and/or the trocar 11 could be linked together, for example, with gears and/or pulleys. The rotational velocities of the spinning the cutter tube 10, the coaxial introducer 54 and/or the trocar 11 could be passively linked together, for example friction between the cutter tube 10 and the coaxial introducer 54 could urge the coaxial introducer 54 to spin with the cutter tube 10.

The cutter tube 10, the coaxial introducer 54 and/or the trocar 11 could have a helical feature on their surface. For example, the coaxial introducer 54 could comprise a rifled surface 14. The rifled surface 14 could be embossed and/or debossed on the surface the coaxial introducer 54. The rifled surface 14 could be on the inside and/or the outside of the coaxial introducer 54. The rifled surface 14 could be clockwise and/or counter-clockwise. The rifled surface 14 could urge the tool 5 distally or proximally as the coaxial introducer 54 is rotated. For example, rotating the coaxial introducer 54 during insertion and/or coring could allow the rifled surface 14 to interact with the tissue and thereby urge the tool distally. Urging, pulling, pushing and/or forcing the tool longitudinally (e.g., distally and/or proximally) could provide the operator with more control while positioning the tool 5, similar to how power-steering provides a vehicle driver with superior handling. The rifled surface 14 could be formed on the surface of the coaxial introducer 54, for example by stamping and/or machining the surface, and/or be a separate material secured to the coaxial introducer 54 (for example by welding, soldering, brazing and/or friction) The rifled surface 14 could be present on the cutter tube 10, the coaxial introducer 54 and/or the trocar 11.

The cutter tube 10, the coaxial introducer 54 and/or the trocar 11 could pulse distally/proximally in the direction of tubular longitudinal axis 8. For example, during insertion, sampling and/or partoff the cutter tube 10, the coaxial introducer 54 and/or the trocar 11 could oscillate to reduce resistance and/or provide superior cutting. The cutter tube 10, the coaxial introducer 54 and/or the trocar 11 could oscillate at an ultrasonic frequency.

A trocar tab 19 may indicate the longitudinal position of the trocar 11 with respect to the cutter tube 10 and/or the handle 6. The trocar tab 19 may be visible in a trocar tab slot 20. The trocar tab slot 20 may be located in the handle 6. The trocar tab slot 20 may be open and/or covered. For example, the trocar tab slot 20 may be a transparent section in the handle 6. The trocar tab slot 20 may have visual and/or tactile position indicators. The indicators on the trocar tab slot 20 may have visual and/or tactile position indicators may be metric and/or English units, for example every 1 cm. The indicators on the trocar tab slot 20 may have visual and/or tactile position indicators may mark approximate sample length. The trocar tab 19 may be adjusted by the operator to control the position of the trocar 11. The trocar tab 19 may be longitudinally and/or rotationally fixed with respect to the trocar 11. The trocar 11 may be secured to the trocar tab 19 and/or they may be separate elements. The length of the trocar 11 extending proximally out of the cutter tube 10 may be an indicator length, such as a first indicator length, that may correspond to the length and/or volume of the tissue in the cutter tube 10.

FIG. 2a illustrates that the cutter tube 10 may have a round cross-section. The cutter tube 10 may be manufactured from stainless steel hypodermic tubing (i.e., hypotube). For example, the cutter tube 10 may be manufactured from full hard 304SS hypotube. The hypotube may be welded and drawn. The hypotube may be ground (e.g., centerless ground and/or plugged and ground).

FIG. 2a illustrates that the trocar 11 may be secured to a trocar support 16. The trocar support 16 may be the trocar tab 19. The trocar support 16 may have different properties than the trocar 11. The trocar 11 and/or the trocar support 16 may be made from hardened 300 or 400 series stainless steel, plastic (e.g., plastic, such as abs, delrin, glass-filled abs, glass filled delrin, ryton, polycarbonate). The trocar support 16 may be secured to the trocar 11 via friction, welding, brazing, soldering, overmolding, snap-fit, adhesive and/or solvent bonding. The trocar support 16 may be made injection molded. The trocar support 16 may be flexible. The outside diameter of the trocar support 16 may be threaded. For example, the position of the trocar support 16 may be controlled by spinning the trocar support 16 with respect to a threaded nut 17. The threaded nut 17 may be secured to the cutter tube 10, the coaxial introducer 54 and/or the trocar 11. For example, rotating the cutter tube 10 clockwise may urge the trocar support 16 and the trocar 11 proximally. For example, rotating the cutter tube 10 counter-clockwise may urge the trocar support 16 and the trocar 11 distally. A portion of the trocar support 16 could be threaded. For example, the distal end of the trocar support 16 could be unthreaded so that when the trocar support 16 is fully proximal, the threads on the trocar support 16 do not engage with the threaded nut 17. The threaded nut 17 could be expandable. The threaded nut 17 could be a split and/or a partial nut. The threaded nut 17 could be moved to control if it is engaged with the trocar support 16.

FIG. 2b illustrates that the trocar 11 may be positioned proximally to the cutter tube terminal distal end 12, thereby creating a tissue sample space 18. The trocar point 13 may extend past the cutter tube terminal distal end 12, such as a first trocar position. The trocar point 13 may be constrained to never extend past the cutter tube terminal distal end 12 and/or the partoff mechanism 31. The tissue sample space 18 may be filled with zero, one or multiple tissue samples. The tissue samples space 18 may be bounded by the trocar 11 on the proximal end. The tissue sample space 18 may be surrounded by the cutter tube 10. The distal end of the tissue sample space 18 may be open or closed; for example, by the partoff mechanism 31. The volume of the tissue sample space 18 may be adjusted. During insertion, the tissue sample space 18 may be non-existent, if the trocar 11 extends distally past the cutter tube terminal distal end 12. During coring, the tissue sample space 18 may be empty, partially filled with tissue and/or completely filled with tissue. For example, the trocar 11 could be urged and/or pushed back by tissue and/or tissue samples, thereby the tissue sample space 18 may expand as necessary to accommodate more tissue samples. The trocar tab 19 and/or the trocar 11 may provide a visual and/or tactile representation of how many tissue samples are located in the cutter tube 10. The trocar tab 19 could disable the first button 22 and/or the second button 7 when it has reached a certain position. When the trocar 11 is fully proximal, the trocar tab 19 could be fully proximal. When the trocar 11 is fully proximal, such as a second trocar position, a portion of the trocar 11 could remain within the cutter tube 10 and/or the trocar 11 could fully exit from the cutter tube 10. For example, when the trocar 11 is fully proximal the tissue samples may exit from the proximal end of the cutter tube 10 into the handle and/or a collection chamber. The trocar 11 could be removed from the cutter tube 10 and/or the handle 6 to allow the operator to access the lumen of the cutter tube 10, for example to use a tissue transport mechanism and/or aspiration and/or a marker. A proximal terminal end of the trocar 11 may always be distal to a proximal terminal end of the handle 6. The trocar 11 and/or the trocar tab 19 could engage or disable the first button 22 and/or the second button 7 based on the position of the trocar 11 and/or the trocar tab 19 with respect to the handle 6 and/or the cutter tube 10. The trocar 11 could be positioned fully proximally during coring, thereby expanding the tissue sample space 18 to the maximum possible volume; the tissue samples could fill the tissue sample space 18 as necessary. The proximal end of the tissue sample space 18 could be open. For example, the trocar 11 could fully exit the cutter tube 10; thereby, allowing the operator to obtain more tissue samples than could fit inside of the cutter tube 10 at one time. The trocar 11 could be advanced distally to push out any samples from the tissue sample space 18. For example, the tool 5 could be removed from the tissue and the tissue samples could exit from cutter tube terminal distal end 12. After the trocar 11 has pushed out tissue samples from the tissue sample space 18, the trocar 11 could be positioned distal to the cutter tube terminal distal end 12 (as shown in FIG. 2*a*) and the tool 5 could be in the insertion state; the operator could then insert the tool into the tissue and obtain additional tissue samples.

FIG. 2*b* illustrates that the tool 5 can be manually advanced into the tissue. The operator may press the first button 22 and/or the second button 7 to place the tool 5 in a coring state. In the coring state, the cutter tube 10 may be spinning. The cutter tube terminal distal end 12 may cut through the tissue as the cutter tube 10 is advanced. The terminal distal end 12 may be sharpened. A tissue sample or tissue samples may enter into the tissue sample space 18. The operator may manually advance the tool 5 through the tissue while the cutter tube 10 is spinning. The operator may control the rate of advancement and total deflection of the cutter tube 10 and/or the tool 5. For example, the the operator may be able to obtain different tissue sample lengths. For example, the operator may advance the tool slowly for safety reasons and/or depending on the tissue type (e.g., hard and/or dense tissues).

FIG. 3 illustrates that a partoff tab 30 may obstruct tissue samples 101*d* and 101*e* from exiting the cutter tube 10. The partoff tab 30 may be a component in the partoff mechanism 31. The partoff mechanism 31 may be used to sever a tissue sample from a tissue site; for example after the tissue sample has been cored (but may still be attached to the tissue site). The partoff mechanism 31 may be a passive and/or active system. For example, the partoff mechanism 31 may be deployable tab, a multi-bar linkage or a passive, spring-loaded tab. The partoff mechanism 31 may be deployed while the spinning about the tubular longitudinal axis 8. The partoff mechanism 31 may be at least one tab that may allow the tissue to move proximally and/or distally along the tubular longitudinal axis 8. The coaxial introducer 54 may control the deployment of the partoff mechanism 31; for example, the axial position of the coaxial introducer 54 and/or the tissue-engaging inner element 100 relative to the cutter tube 10 may control the position of the partoff mechanism 31. A tissue-engaging inner element 100 may be located inside of the cutter tube 10. For example, the tissue-engaging inner element 100 may be helically shaped. The tissue-engaging inner element 100 may be made from stainless steel. The tissue-engaging inner element 100 may be rotationally stationary/fixed or spin with respect to the cutter tube 10. The tissue-engaging inner element 100 may be rotationally stationary and/or rotate with respect to the handle 5. The tissue-engaging inner element 100 may be longitudinally fixed and/or move relative to the handle 5 and/or the cutter tube 10. The tissue samples 101*d* and 101*e* may contact the tissue-engaging inner element 100 and/or the cutter tube 10. For example, the cutter tube 10 may urge tissue samples 101*d* and 101*e* to spin. For example, the tissue samples 101*d* and 101*e* may spin relative to the tissue-engaging inner element 100. The relative rotation between the tissue samples 101*d* and/or 101*e* and the tissue-engaging inner element 100 may urge the tissue samples proximally and/or distally relative to the handle 5. For example, while advancing the tool 5 into the tissue, the cutter tube 10 may be spinning (e.g., spinning relative to the handle 5 and/or the tissue) and may be coring tissue samples 101*d* and/or 101*e* and may be positioning them inside of the tissue sample space 18. The relative rotation between the tissue sample(s) 101*d* and/or 101*e* and the tissue-engaging inner element 100 may urge/pull/force the tissue further into the cutter tube 10; for example, creating a mechanical suction force to obtain larger tissue sample(s)/Old and/or 101*e*. Transporting the tissue samples 101*d* and/or 101*e* proximally inside of the cutter tube 10 may create a vacuum, thereby drawing more tissue into the cutter tube 10. A vacuum may be applied while sampling and/or advancing the tool to urge tissue into the cutter tube 10. For example, the handle 6 and/or the cutter tube 10 may be longitudinally stationary while a vacuum is applied to the proximal end of the cutter tube 10. The vacuum may urge tissue into the cutter tube 10, which may be cored and/or cut while the cutter tube 10 is spinning.

FIG. 3 illustrates that the tissue sample 101*d* may be acquired first (e.g., coring into the tissue mass and then parting off the tissue sample from the tissue mass). The subsequent tissue sample 101*e* may be acquired from the same tissue mass or a different tissue mass. As the tissue sample 101*e* is cored, it may push the first tissue sample 101*d* proximally towards the handle. The samples may be stored sequentially/chronologically in the order they were acquired. The samples may be removed by pushing them out with a rod. The samples may be removed by hydraulic, pneumatic pressure and/or vacuum. The partoff tab 30 may be left in the actuated position to prevent the tissue samples 101 from exiting from the distal end 12.

FIG. 3 illustrates that the tissue-engaging inner element 100 may be located within the cutter tube 10. The tissue transport system 100 may comprise an elongated coil. The tissue-engaging inner element 100 may be rotationally stationary relative to the handle 6. The tissue-engaging inner element 100 may terminate proximal to the partoff tab 30. The tissue-engaging inner element 100 may terminate approximately 2-3 cm proximal to the partoff tab 30. The tissue-engaging inner element 100 may engage with tissue sample 101*d* after a second tissue sample 101*e* pushes the tissue sample 101*d* into contact with the tissue-engaging inner element 100. For example, the operator may first acquire a tissue sample 101*d*. The operator may then acquire the second tissue sample 101*e*, which subsequently pushes the tissue sample 101*d* proximally and into contact with the tissue-engaging inner element 100. Once the tissue sample 101d is engaged with the tissue-engaging inner element 100, the tissue sample 101d may be transported proximally into the handle 6. For example, if the tissue sample 101d is rotating relative to the tissue-engaging inner element 100, it may be urged proximally (e.g., a corkscrew effect). The tissue-engaging inner element 100 may extend fully to the partoff tab 30 such that the tissue sample 101d is immediately in contact with the tissue-engaging inner element 100 without requiring the second tissue sample 101e to push the tissue sample 101d proximally. The tissue-engaging inner element 100 may translate relative to the cutter tube 10; for example, the transport system 100 may oscillate proximally/distally by 0.5 to 1 mm.

FIG. 4 and FIG. 5 illustrate that the handle 6 could feature a reusable handle 50. The reusable handle 50 and/or the handle 6 could include at least one of a motor, switch, power jack, battery, LED, PCB, resistor, circuit, capacitor, nitinol actuator, shape memory actuator, muscle wire, spring and/or string. The trocar 11 and/or the trocar tab 19 could be visible in the handle 6. The trocar 11 and/or the trocar tab 19 could be controlled using the first button 22 or another button (not shown). The trocar 11 could be pushed proximally by a tissue sample 101. The trocar 11 could be pushed and/or pulled manually, automatically or semi-automatically. For example, the operator could push the trocar 11 and/or the trocar tab 19 distally. The operator could turn a wheel and/or a thumb wheel which could engage the trocar 11 and/or the trocar tab 19; for example, the thumb wheel could contact the trocar 11 and/or the trocar tab 19 with friction or a rack/pinion mechanism. The thumb wheel could be geared to ensure optimize the level of torque and/or manipulation required. The tissue indicator could be straight, the trocar tab slot 20 is shown or it could be a different shape and/or mechanism. For example, the trocar tab slot 20 could be round and/or spiral. The tissue indicator could be a dial indicator that could be driven by the trocar 11 and/or the trocar tab 19. For example, a string or wire could be connected between the trocar tab 19 and/or the proximal end of the trocar 11 and/or an indicator (e.g., a dial indicator and/or the trocar tab slot 20). A string or wire could be connected between the trocar tab 19 and/or the trocar 11 and a rotary and/or linear actuator. For example, a string or wire could be connected to both a pulley and the trocar tab 19 and/or the trocar 11; rotating the pulley could pull on the string and therefore force the trocar point 13 distally; the pulley could be driven manually and/or using an actuator, such as a motor. A second motor (in addition to the motor used to spin the cutter tube 10) could be used to actuate the trocar tab 19 and/or the trocar 11. Forcing the trocar 11 distally could push tissue samples out of the cutter tube terminal distal end 12. The trocar 11 and/or the trocar tab 19 could be manipulated using various actuators, including a brushed motor, a brushless motor, a spring, and/or a shape memory actuator. The handle 6 could contain two buttons: one button could be used for coring the tissue and the other button could be used for advancing the position of the trocar 11. During coring, the trocar 11 could be pushed back by tissue samples or using an actuator built into the tool 5. The trocar 11 and/or the trocar point 13 can spin with the cutter tube 10 to minimize trauma to any tissue samples.

FIG. 6 illustrates that the reusable handle 50 could be battery and/or wall-powered (e.g., tethered). The reusable handle could be sealed from the patient and patient tissue/fluids to prevent cross-contamination. For example, seals and/or magnets (e.g., non-contact actuation) can be used to prevent the reusable handle from engaging with patient tissue directly or indirectly. The reusable handle may contain a first hub 51 and a second hub 52. The first hub 51 and/or the second hub 52 may engage with interlocking hubs on the disposable handle. The first hub 51 and/or the second hub 52 may be driven using the same actuator or different actuators. The first hub 51 and/or the second hub 52 may use one-way clutches so that the first hub 51 and/or the second hub 52 may be driven in only one direction. For example, spinning a motor clockwise may drive only the first hub 51 while driving the motor counter-clockwise may drive only the second hub 52 (or vice-versa). Alternatively, one hub may always be driven, whereas the other hub may be only driven in one direction. A speed reducer and/or gear head may be used to adjust the speed and/or torque of one hub versus the other hub.

The coaxial introducer 54 and/or the cutter tube 10 may be longitudinally fixed with respect to the handle 6. The coaxial introducer 54 and/or the cutter tube 10 may be partially longitudinally fixed with respect to the handle 6. For example, during tissue coring, the coaxial introducer 54 and/or the cutter tube 10 may be advanced or retracted between 0.01 in (0.25 mm) and 1 in (2.5 cm), for example 0.06 in (1.5 mm) and remain longitudinally fixed with respect to the handle 6 while the tool is manually advanced into the tissue. Upon completion of coring, the coaxial introducer 54 and/or the cutter tube 10 may be retracted or advanced. The cutter tube 10 may continue to spin after the first button 22 and/or another button is released; for example the cutter tube 10 may continue to spin 0.01 to 30 seconds, such as approximately 0.5 or 1 second. Depressing the first button 22 may adjust the partoff mechanism 31 to the coring state and then spin the cutter tube 10. Releasing the cutter tube 10 may adjust the partoff mechanism 31 into the partoff state, keep the cutter tube spinning for a pre-determined or user-dependent time period such as 0.5 seconds to complete tissue partoff/severing/cutting and then stop the cutter tube 10 from spinning. Manipulating the axial position of the coaxial introducer 54 and the cutter tube 10 with respect to each other may allow the cutter tube 10 to continue spinning while preventing the cutter tube terminal distal end 12 from coring additional tissue. For example, after coring a tissue sample, the cutter tube 10 may continue to spin to partoff the tissue sample from the tissue mass and/or transport the tissue sample (e.g., using a helical transport element); adjusting the linear position of the cutter tube 10 with respect to the coaxial introducer 54 may hide the cutter tube terminal distal end 12 within the coaxial introducer 54 to ensure that no additional tissue is cored and/or traumatized. The coaxial introducer 54 may be rotationally fixed with respect to the handle 6 and/or the tissue. The coaxial introducer 54 may rotate with or with respect to the cutter tube 10.

FIG. 7 illustrates that a trocar tube 120 may be positioned concentrically over the trocar 11. The trocar tube 120 may be a clearance fit with the trocar 11, for example with a gap of less than 0.01 in, approximately, 0.005 inches. The trocar 11 may be longitudinally moveable and/or fixed with respect to the trocar tube 120. The trocar 11 may be rotationally moveable and/or fixed with respect to the trocar tube 120. During insertion of the tool 5 into the tissue, the trocar point 13 may extend distal to a trocar tube distal end 121. During tissue acquisition, the trocar point 13 may be recessed proximally to the trocar tube distal end 121; thereby protecting the trocar point 13 and minimizing trauma to the tissue samples that could be created by the trocar point 13. A flexible and/or a slit seal could be placed on the distal end of the trocar tube to minimize contact between the trocar point 13 and tissue samples. The trocar tube distal end 121 could be in contact with the tissue samples 101 during tissue acquisition and when pushing the tissue samples 101 out of the cutter tube 10.

FIG. 8 illustrates that an inner tube 125 may be located concentrically within the cutter tube 10. The inner tube 125 may have a dull or a sharp end. The inner tube 125 may be rotationally and/or longitudinally fixed with respect to the cutter tube 10. The inner tube 125 may rotate or move with respect to the cutter tube 10. The inner tube 125 may have a clearance fit with the cutter tube 10, with a gap of less than 0.02 inches between the walls, for example 0.003 inches. The inner tube 125 may be proximal to the cutter tube terminal distal end 12 during coring and distal to the coring tube distal end 12 when the tool 5 is not coring. The tool 5 can be used with different imaging systems, including ultrasound, stereotactic, MRI, x-ray tomography and/or tomosynthesis. The tool 5 can be advanced manually, automatically or semi-automatically. The tool 5 can be used to capture tissue samples of variable lengths. When used manually (e.g., under ultrasound guidance), the operator may visualize the tool 5 cutting through the tissue and obtain the ideal length of tissue required. When used manually (e.g., under ultrasound guidance), the operator may visualize the tool 5 cutting through the tissue and ensure that the tool 5 does not cause unnecessary patient trauma; for example, if the operator realizes that the tool 5 is about to enter an undesired tissue, the operator can release a button on the tool 5 and/or stop advancing the tool 5. The first button 22 can be depressed and/or moved axially, thereby allowing additional functionality with a single button. For example, depressing the first button 22 may control the rotation of the cutter tube 10 and pushing the first button 22 forward and/or backward may control the partoff mechanism 31. Manipulating the first button 22 to the left and/or right may control the position of the trocar 11. Depressing the first button 22 may control the rotation of the cutter tube 10 and pulling the first button 22 backward may control the partoff mechanism 31 and pushing the first button 22 forward may control the position of the trocar 11. A knob and/or button may be used to control the position of the cutter tube 10 with respect to the handle 6. For example, spinning a knob may advance the cutter tube 10 distally while holding the handle 6 stationary, thereby offering precise control of the cutter tube terminal distal end 12 without having to manipulate the handle 6 with respect to the tissue. Depressing the first button 22 may cause the cutter tube 10 to be advanced distally at a pre-determined rate (such as 0-2 cm per second, approximately 1 cm/sec) and/or distance (such as 1, 2 or 3 cm) and releasing the first button 22 may cause the cutter tube 10 to retract into the handle 6. In the default, standby position the cutter tube terminal distal end 12 may be proximal to a distal end of the coaxial introducer 54 or the inner tube 125, thereby sheathing the sharp end of the cutter tube terminal distal end 12. During coring and as the cutter tube 10 is spinning, the cutter tube terminal distal end 12 may be positioned distal to a distal end of the coaxial introducer 54 or the inner tube 125, thereby allowing the cutter tube terminal distal end 12 to be in contact with the tissue. Sheathing and unsheathing the cutter tube terminal distal end 12 may protect both the cutter tube terminal distal end 12 and the patient from unnecessary and/or unintended trauma. A light, such as and LED or electroluminescent material may be used in the tool 5. The light may be used to illuminate the tissue, the buttons, the trocar 11 and/or the trocar tab 19. A digital indicator may be used to indicate the position of the trocar point 13. The distance and/or angular position between the trocar point 13 and the trocar tab 19 may be fixed or variable. For example, the trocar point 13 and the trocar tab 19 could be made from the same material (e.g., an injection molded component). The trocar tab 19 could be a separate component that can be used to push the trocar point 13 distally but not be able to apply proximal force to the trocar point 13. The proximal end of the trocar 11 may be used to indicate the position of the trocar point 13 instead of the trocar tab 19.

FIG. 9 illustrates that the second button 7 could be slideable within a button track 201. The button track 201 could extend for the entire length of the handle 6 or a portion of the handle 6. The second button 7 can slide within the button track 201, for example between a first button track position 202a and a second button track position 202b. The second button 7 may engage directly and/or indirectly with the trocar 11. For example, the button 7 could feature a one-way clutch mechanism. Many versions of one-way clutch mechanisms exist, including those found in ratchets, clamps, speed clamps and one-way bearings. An example of a one-way clutch mechanism could be a piece of sheet metal, for example between 0.005 in (0.13 mm) to 0.060 in (1.5 mm) thick, such as ~0.02 in thick (0.5 mm) with a hole and/or slot cut into the strip that the trocar 11 may slide through; the angle of the sheet metal strip may be such that the sheet metal may bind with the trocar 11 in one direction but be unbound in a second direction. For example, the sheet metal strip may be at an angle of 5-60 degrees with respect to a front plane, such as 15 and/or 20 degrees. The front plane may be perpendicular to the tubular longitudinal axis 8. Another one-way clutch mechanism may include two ball bearings on opposite sides of the trocar 11 that are housed within a ramped slot(s), such that the ball bearings squeeze against the trocar 11 and bind the trocar 11 when it slides in one direction, but disengage when the trocar 11 moves in the other direction. Sliding the second button 7 between the first button track position 202a and the second button track position 202b may push the trocar 11 distally. The second button 7 may be slid repeatedly between button track positions 202a and 202b to move the trocar 11 distally until it exits the cutter tube terminal distal end 12. A third button track position 202c may allow the second button 7 to engage with an unlocking post 200. The unlocking post 200 may disable the one-way clutch in the second button 7, thereby allowing the trocar 11 to slide freely proximally, distally and/or rotationally. For example, when coring and/or obtaining tissue, the second button 7 may be in the third button track position 202c, thereby engaging with the unlocking post 200 and allowing tissue samples 101 to push proximally on the trocar 11 and therefore translate the trocar 11 proximally. The trocar 11 may be visible through the button track 201 and/or the handle 6, thereby providing an indication of how much tissue is located within the cutter tube 10. The operator may then remove the device from the tissue site and remove the tissue samples 101 from the cutter tube 10 by sliding the second button 7 back and forth between button track positions 202a and 202b. A button locking feature may be present to limit the motion of the second button 7 between the button track positions 202a and 202b; the button locking feature may be disengaged by depressing the first button 22. The button locking feature may be used to ensure that the second button 7 does not contact the unlocking post 200. During insertion of the tool 5 into the tissue site, the button locking feature may be used to ensure that the second button 7 is binding the trocar 11 such that it does not slip proximally into the cutter tube 10. The button locking feature may lock the second button 7 and/or the trocar 11, such as the terminal proximal end of the trocar 11. The button locking feature may use the trocar 11 as a guide, such that the button locking feature locks the second button 7 and/or the trocar 11 once the trocar 11 has reached a certain position, such as when the trocar point 13 is extending past the cutter tube terminal distal end 12. The second button 7 may include a button ramp 205 which may engage directly and/or indirectly with the first button 22 and/or the partoff mechanism 31. For example, when advancing the trocar 11 distally, the button ramp 205 may force the first button 22 into a position where the partoff mechanism 31 is hidden and/or retracted (e.g., in the coring state and/or configuration), thereby allowing tissue samples 101 to exit from the cutter tube 10. For example, the button ramp 205 could prevent the first button 22 from being fully depressed and therefore spinning the cutter tube 10. The trocar 11 could be removed entirely from the handle 6. One or more springs may be used, for example to bias the second button 7 proximally. If the trocar 11 is removed from the handle 6 or is moved proximally such that it does not engage with the cutter tube 10, tissue samples 101 may enter a sample collection space 210. The sample collection space 210 may be a collection chamber. The proximal end of the trocar 11 may have a larger diameter and/or a lip. For example, the proximal 0.02 in (0.5 mm)-0.8 in (2 mm) of the trocar 11, such as 0.1 in (2.5 mm) in length may have a larger major diameter than the remainder of the trocar. The proximal lip of the trocar 11 may be formed by deforming the trocar 11, for example by clamping, crimping and/or swaging. The proximal lip of the trocar 11 may be formed by securing another component to the trocar 11 such as a thin-walled tube, which could be glued, crimped, press-fit, brazed, welded, soldered or mechanically fastened to the trocar 11. The proximal lip of the trocar 11 may engage with the cutter tube 10, the handle 6 and/or the second button 7 to prevent the trocar 11 from advancing to far distally. The proximal lip of the trocar 11 may allow the trocar 11 to spin freely with respect to the handle 6. The trocar 11 could be transported using a cable, thread, wire, electromechanically, electromagnetically, magnetically, pneumatically, hydraulically, with a vacuum, with a spring and/or manually (e.g., by manually pushing and/or pulling on the trocar). The sheet metal strip may be formed by stamping, laser-cutting, metal injection molding, water-jet cutting, machining, plasma cutting, etching and/or cutting. The button track 201 may be the trocar tab slot 20.

The tissue samples can be transported using a helical transport system (e.g., a stationary coil) and/or with additional systems. For example, a second tube can be located concentrically within the cutter tube 10 and be pulled proximally. The second tube can have adjustable and/or one-way locking features to engage or secure the tissue samples 101. The second tube may be the same as the inner tube 125. One-way locking features may include tabs that are bent inwards and allow the tissue samples 101 to move proximally, but not distally. The coil may be moved proximally with or without tissue samples 101. A vacuum may be used to pull tissue samples 101 proximally. The trocar 11 may be flexible. The trocar 11 may wrap around a pulley, which may be turned to advance and/or retract the trocar 11; the angular position of the pulley may be used to indicate the position of the trocar point 13. The trocar 11 may be flexible and be located within a contoured guide within the handle 6 or an empty space within the handle 6. The trocar 11 may extend past the handle 6, for example proximal to the handle 6 and/or trocar tab slot 20. A compression, tension, torsion, clock and/or power spring may be used to bias the trocar 11 in a distal and/or proximal direction. A ratchet mechanism may be used to advance or retract the trocar 11. For example, a button and/or knob may be pushed forward from the default position 0.1 to 3 inches, for example 0.75 in to advance the trocar 11 and then retract to the default position with a spring; adjusting the position of the trocar 11 during the manual pushing step but without adjusting the position of the trocar 11 during the retracting step.

The internal diameter of the cutter tube 10 may be larger than about 0.04 in (1.0 mm), yet more narrowly larger than about 0.06 in (1.5 mm), yet more narrowly larger than about 0.08 in (2.0 mm), yet more narrowly larger than about 0.1 in (2.5 mm), yet more narrowly larger than about 0.12 in (3.0 mm), yet more narrowly larger than about 0.14 in (3.5 mm) or yet more narrowly larger than about 0.16 in (4.0 mm). The internal diameter of the cutter tube 10 may be less than about 0.16 in (4.0 mm), or yet more narrowly smaller than about 0.14 in (3.5 mm), or yet more narrowly smaller than about 0.12 in (3.0 mm), or yet more narrowly smaller than about 0.10 in (2.5 mm), or yet more narrowly smaller than about 0.08 in (2.0 mm), or yet more narrowly smaller than about 0.06 in (I 0.5 mm) or yet more narrowly smaller than about 0.04 in (1.0 mm).

The wall thickness of the cutter tube 10 may be larger than about 0.002 in (0.05 mm), or yet more narrowly larger than about 0.004 in (0.10 mm) or yet more narrowly larger than about 0.006 in (0.15 mm). The wall thickness of the cutter tube 10 may be smaller than about 0.006 in (0.15 mm), or yet more narrowly smaller than about 0.004 in (0.10 mm) or yet more narrowly smaller than about 0.002 in (0.05 mm). The wall thickness of the cutter tube 10 may vary. For example, the partoff tab 30 may have a different wall thickness than the actuator 32.

The cutter tube 10 or any or all elements of the tool and/or other tools or apparatuses described herein can be made from or coated with, for example, single or multiple stainless steel alloys, steel, spring steel, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy), tungsten-rhenium alloys, polymers such as polyethylene teraphathalate (PET), polyester (e.g., DACRON® from E. I. Du Pont de Nemours and Company, Wilmington, Del.), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), Parylene poly(p-xylylene) polymers, Parylene N, Parylene C, Parylene D, expanded PTFE (ePTFE), polyether ketone (PEK), polyether ether ketone (PEEK), polycarbonate (PC), Acrylonitrile Butadiene Styrene (ABS), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), Nylon, Vinyl, polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized powder, osteogenic powder, beads of bone), a material with high strength (60 ksi) and biocompatibility, any of the other materials listed herein or combinations thereof. Examples of radiopaque materials are barium sulfate, zinc oxide, titanium, stainless steel, nickel-titanium alloys, tantalum and gold. The device can be made from substantially 100% PEEK, braided nylon, braid reinforce nylon, braid reinforced polyimide, braid reinforced tubing, substantially 100% titanium or titanium alloy, or combinations thereof.

The cutter tube 10 may spin or rotate at a velocity relative to the handle 6 of greater than about 100 rpm, yet more narrowly larger than about 1,000 rpm, yet more narrowly larger than about 2,500 rpm, yet more narrowly larger than about 3,000 rpm, yet more narrowly larger than about 4,000 rpm, yet more narrowly larger than about 5,000 rpm, yet more narrowly larger than about 7,500 rpm, yet more narrowly larger than about 10,000 rpm. The cutter tube 10 may spin or rotate at a velocity relative to the handle 6 of less than about 10,000 rpm, yet more narrowly less than about 7,500 rpm, yet more narrowly less than about 5,000 rpm, yet more narrowly less than about 4,000 rpm, yet more narrowly less than about 3,000 rpm, yet more narrowly less than about 2,500 rpm, yet more narrowly less than about 1,000 rpm, yet more narrowly less than about 100 rpm.

The internal diameter of the cutter tube 10 may be larger than about 0.5 mm (0.02 in), more narrowly larger than about 1 mm (0.04 in), yet more narrowly larger than about 1.5 mm (0.06 in), yet more narrowly larger than about 2 mm (0.08 in), yet more narrowly than about 2.5 mm (0.10 in), yet more narrowly larger than about 3 mm (0.12 in), yet more narrowly larger than about 3.5 mm (0.14 in), yet more narrowly larger than about 4 mm (0.18 in), yet more narrowly larger than about 4.5 mm (0.18 in), yet more narrowly larger than about 5 mm (0.20 in), yet more narrowly larger than about 6 mm (0.24 in), yet more narrowly larger than about 7 mm (0.28 in), or yet more narrowly larger than about 10 mm (0.39 in). The internal diameter of the cutter tube 10 may be less than about 10 mm (0.39 in), more narrowly less than about 7 mm (0.28 in), yet more narrowly less than about 6 mm (0.24 in), yet more narrowly less than about 5 mm (0.20 in), yet more narrowly less than about 4.5 mm (0.18 in), yet more narrowly less than about 4 mm (0.18 in), yet more narrowly less than about 3.5 mm (0.14 in), yet more narrowly less than about 3 mm (0.12 in), yet more narrowly less than about 2.5 mm (0.10 in), yet more narrowly less than about 2 mm (0.08 in), yet more narrowly less than about 1.5 mm (0.06 in), yet more narrowly less than about 1 mm (0.04 in), or yet more narrowly less than about 0.5 mm (0.02 in).

The wall thickness of the cutter tube 10 may be larger than about 0.05 mm (0.002 in), more narrowly larger than about 0.10 mm (0.004 in), yet more narrowly larger than about 0.15 mm (0.006 in), yet more narrowly larger than about 0.20 mm (0.008 in), yet more narrowly larger than about 0.30 mm (0.012 in), yet more narrowly larger than about 0.50 mm (0.020 in), yet more narrowly larger than about 0.70 mm (0.028 in), or yet more narrowly larger than about 1.00 mm (0.039 in). The wall thickness of the cutter tube 10 may be less than about 1.00 mm (0.039 in), yet more narrowly less than about 0.70 mm (0.028 in), yet more narrowly less than about 0.50 mm (0.020 in), yet more narrowly less than about 0.43 mm (0.017 in), yet more narrowly less than about 0.30 mm (0.012 in), yet more narrowly less than about 0.20 mm (0.008 in), yet more narrowly less than about 0.15 mm (0.006 in), yet more narrowly less than about 0.10 mm (0.004 in), or yet more narrowly less than about 0.05 mm (0.002 in).

Multiple tissue samples can be collected and/or obtained and/or parted-off without removing the tool from the mass of tissue (i.e., tissue mass). The tubular longitudinal axis 8 can pass through the cutter tube 10, the transport system 100 and/or the handle 6. The cutter tube terminal distal end 12 may be sharpened mechanically, electro-chemically and/or chemically. The trocar 11 may slide in the cutter tube 10 and/or the handle 6. The first button 22 and/or the second button 7 may contact the trocar 11 and/or the trocar tab 19. There may be sufficient friction between the trocar 11 and another component in the tool 5 (such as the cutter tube 10, the first button 22, the handle 6 and/or the second button 7) to prevent the trocar 11 from moving relative to the handle 6 because of gravity; however, the friction may be low enough to allow the tissue samples 101 to urge the trocar 11 proximally. The frictional force may be adjustable; for example, the friction between the trocar 11 and another component in the tool 5 (such as the cutter tube 10, the first button 22, the handle 6 and/or the second button 7) may be lower when the first button 22 and/or the second button 7 are depressed than when no buttons are depressed. The frictional force between the trocar 11 and another component in the tool 5 (such as the cutter tube 10, the first button 22, the handle 6 and/or the second button 7) may be between 0.01 and 2 Newtons.

The trocar 11 may be slidably positioned inside of the cutter tube 10. The handle may be longitudinally fixed with respect to the cutter tube 10. The cutter tube 10 may be a coring element. The trocar 11 may be an indicator. For example, the trocar 11 may be string, a liquid and/or some other material that may be displaced by the tissue samples 101 in the cutter tube 10.

PCT/US 2014/052,431 filed Aug. 26, 2014; U.S. application Ser. No. 14/517,873 filed Oct. 19, 2014; PCT/US11/061,089 filed Nov. 16, 2011; U.S. Pat. No. 8,317,727 filed on Apr. 21, 2012; U.S. Provisional Application Nos. 61/872,678, filed Aug. 31, 2013; 62/086,523, filed on Dec. 2, 2014; 61/872,674, filed Aug. 31, 2013 are all incorporated by reference herein in their entireties.

It is apparent to one skilled in the art that various changes and modifications can be made to this disclosure, and equivalents employed, or combinations of any of the disclosed elements, characteristics, features, devices, tools, steps, or methods without departing from the spirit and scope of the invention. Any of the disclosed elements, characteristics, features, devices, tools, steps, or methods can be present as a singular or as a plurality regardless of whether the elements, characteristics, features, devices, steps, or methods are explicitly disclosed herein as being singular or as a plurality. Elements shown with any variation are exemplary for the specific variation and can be used on other variation within this disclosure.

I claim:

1. A tool for acquiring a tissue comprising:
    a cutter tube for receiving the tissue;
    a handle, wherein the cutter tube is configured to rotate with respect to the handle about a longitudinal axis of the cutter tube;
    a trocar co-axially disposed within the cutter tube; and
    an indicator configured to indicate the amount of tissue in the cutter tube, wherein the indicator comprises a tab coupled to the trocar and disposed within a tab slot located in the handle, wherein the tab is longitudinally displaceable within the tab slot and restricted from rotating about a longitudinal axis of the handle by the tab slot, and wherein the trocar is restricted from rotating about the longitudinal axis of the cutter tube.

2. The tool of claim 1, wherein the indicator comprises a first indicator length extending out of the cutter tube, and wherein the first indicator length corresponds to the length of the tissue in the cutter tube.

3. The tool of claim 1, wherein a partoff mechanism is located adjacent to the cutter tube.

4. The tool of claim 3, wherein the partoff mechanism is configured to sever the tissue.

5. The tool of claim 1, wherein the indicator is configured to rotate with respect to the handle.

6. The tool of claim 1, wherein the cutter tube is longitudinally fixed with respect to the handle.

7. The tool of claim 1, wherein the indicator is configured to eject the tissue from the cutter tube.

8. The tool of claim 1, wherein the tab slot comprises tactile position indicators to indicate the amount of tissue in the cutter tube.

9. The tool of claim 1, wherein the tab slot extends longitudinally along the handle.

10. The tool of claim 1, wherein the slot is covered by a transparent portion of the handle.

11. The tool of claim 1, wherein the tab is adjustable in the tab slot by an operator.

* * * * *